(12) United States Patent
Alcindor

(10) Patent No.: US 11,896,776 B2
(45) Date of Patent: Feb. 13, 2024

(54) URINARY CATHETER WITH INTEGRATED COIL

(71) Applicant: Anthony Alcindor, New York, NY (US)

(72) Inventor: Anthony Alcindor, New York, NY (US)

( * ) Notice: Subject to any disclaimer, the term of this patent is extended or adjusted under 35 U.S.C. 154(b) by 0 days.

(21) Appl. No.: 17/451,361

(22) Filed: Oct. 19, 2021

(65) Prior Publication Data

US 2023/0117722 A1    Apr. 20, 2023

(51) Int. Cl.
*A61M 25/00* (2006.01)

(52) U.S. Cl.
CPC ...... *A61M 25/0017* (2013.01); *A61M 25/005* (2013.01)

(58) Field of Classification Search
CPC ............ A61M 25/0017; A61M 25/005; A61M 27/00; A61M 2210/1078; A61M 2025/0025; A61M 25/04; A61M 2210/1085; A61M 2210/1089; A61M 2202/0496; A61M 25/0021; A61F 5/44; A61F 5/4404; A61F 5/451; A61F 2/0009
See application file for complete search history.

(56) References Cited

U.S. PATENT DOCUMENTS

| | | |
|---|---|---|
| 3,683,928 A | 8/1972 | Kuntz |
| 4,571,241 A | 2/1986 | Christopher |
| 4,813,925 A | 3/1989 | Anderson, Jr. et al. |
| 5,181,911 A | 1/1993 | Shturman |
| 5,569,219 A | 10/1996 | Hakki et al. |
| 5,779,670 A | 7/1998 | Bidwell et al. |
| 5,941,823 A | 8/1999 | Chait |
| 7,766,899 B2 | 8/2010 | Bolmsjo et al. |
| 9,427,552 B2 | 8/2016 | Engelhardt |
| 9,682,220 B2 | 6/2017 | Schertiger et al. |
| 10,300,244 B2 | 5/2019 | Adler et al. |
| 2003/0181842 A1* | 9/2003 | Gellman ............. A61M 27/008 623/1.36 |
| 2005/0171496 A1 | 8/2005 | Guldfeldt et al. |
| 2007/0005024 A1 | 1/2007 | Weber et al. |
| 2007/0225688 A1* | 9/2007 | Goodwin .......... A61M 25/0017 604/327 |
| 2007/0244468 A1 | 10/2007 | Kostandaras |
| 2011/0087181 A1* | 4/2011 | Bidwell ................ A61F 5/4404 604/328 |
| 2011/0307069 A1 | 12/2011 | Frassica et al. |
| 2015/0051588 A1 | 2/2015 | Miller et al. |
| 2018/0264226 A1* | 9/2018 | Erbey, II ................. A61M 1/70 |

FOREIGN PATENT DOCUMENTS

WO    WO-2018075464 A1 *  4/2018  ............... A61F 5/44

* cited by examiner

*Primary Examiner* — Nicholas J. Weiss
*Assistant Examiner* — Brandon W. Levy
(74) *Attorney, Agent, or Firm* — Fish & Richardson P.C.

(57) ABSTRACT

The subject matter of this specification can be embodied in, among other things, an indwelling catheter with an integrated coil section. The coil section, in use, is disposed outside of the urethra and can stretch and bend to accommodate various activities of a user by reducing frictional forces and trauma within the urethra. This improved catheter design results in an increase in range of motion and a decrease in pain for the user.

16 Claims, 2 Drawing Sheets

URINARY CATHETER WITH INTEGRATED COIL

BACKGROUND OF THE INVENTION

The present invention relates to improvements in medical instruments and, more particularly, to a urinary catheter with an integrated coil to improve range of motion thereof.

The average age of the United States population will be over 50 by 2021 or 2022, with 1 in 5 men having some form of prostate issue. Problems of prostate growth include weak stream, stopping and starting, urgency, frequency, pain, waking up and possible sexual dysfunction.

Common reasons to have an indwelling (inside the body) catheter are urinary incontinence (leakage), urinary retention (not being able to urinate), a surgery that made the catheter necessary, or other health problem. Prostate cancer, the second largest killer of men with heart disease being the first, to Benign prostatic hyperplasia (BPH), leads to the essential use of a catheter and the numbers are only increasing. BPH—also called prostate gland enlargement—is a common condition as men get older, there is a second growth. An enlarged prostate gland can cause uncomfortable urinary symptoms, such as blocking the flow of urine out of the bladder. It can also cause bladder, urinary tract or kidney problems.

Statistics show that there are some medical reasons for the second increase in prostate growth, the first being in puberty. However, much is still unknown about exponential second growth that leads to urination problems, including BPH. Urologists refer to this lack of information as idiopathic. Recent data shows that the second prostate growth can now start as early as in the 30's. This is no longer an old man's issue and will prove to be a crisis if millions of younger men are now relegated to urinary catheter use for a period of time. Immobility from the pain caused will directly impact the user not only physically and mentally but also their job, financial security, mental health and all those around him No major advances have been made to the design of the catheter since the introduction of the Foley or Indwelling catheter in 1937. Conventional catheters, although highly functional, are painful and can easily cause trauma to the urethra and bladder. In particular, conventional catheters make basic tasks such as sitting, tying shoes, and walking, sleeping, and exercising painful or impossible. This is due, in part, to back and forth friction of the part of the catheter that is inside the urethra. Complications, such as these, can lead to other issues besides the physical ones mentioned, such as depression. Research and development continue to improve the voiding of urine from the bladder by use from a urinary catheter, the materials it's made from, urine receptacle or bag and ease of insertion through pre-lubrication but nothing, prior to the present invention, has been created/designed to improve mobility and range of motion for individuals using a catheter.

As can be seen, there is a need for an improved urinary catheter with an integrated coil. Through research and development of embodiments of the present invention, it was determined that, by incorporating tubular coils to an indwelling catheter, an increase in range of motion and a decrease in pain can be achieved by reducing the amount of friction and reducing trauma/pain to the urethra.

SUMMARY OF THE INVENTION

Embodiments of the present invention have been developed with consideration taken for the user's mobility and its effect on daily life over a long period of time. Prior to the present invention, advancements in catheter design and manufacturing have focused solely on ease of insertion, bacterial decreases, securement, and materials. Similarly, a urologist's primary goal is to shorten the use of an indwelling catheter by use of medications and/or surgery to avoid infection and trauma.

Consequently, other than the present invention, there has been no consideration from either side (catheter manufacturer and urologist) on how the user must function daily with a catheter for a period of time. In many cases, this can be what the industry calls "long term" need, which is a duration of 30 days or more. Thirty, sixty, ninety days or more is a substantial time to have an impact on a person's life, physically, mentally, emotionally and financially. This substantiates the claim and need for revisions to the traditional indwelling catheter design and the development, manufacturing and use of the integrated coil of the present invention.

The current catheter invention historically has had few advancements since its introduction some 90 years ago (as of the date of filing of the present disclosure) and is regarded by medical practitioners as the top solutions for voiding the bladder of urine due to disfunction or disease, besides the suprapubic catheter which comes out of the lower abdomen rather than the genital area.

Now, with the present invention herein detailed, mobility, pain reduction, range of motion, and physical activities from simply tying shoes to biking, can now be implemented back into the catheter user's lifestyle, thereby offering a semblance of a normal life pre-diagnosis. Studies show that physical and mental health is indeed linked to the quality of life. Both are essential and often during a health crisis, in this case, the inability to urinate properly, the adverse effects have devastating and lasting effects on a person's life. No matter the length of the time life is under duress, any solution that regains balance to quality of life becomes even more important.

The present invention exponentially improves mobility for activity and quality of life by allowing the catheter user range of motion (ROM) without agonizing and debilitating pain. It substantially decreases the friction caused by the in and out movement during daily activities, along the urinary tract caused by traditional catheters, thereby reducing the agonizing pain of a foreign object in the penis/urethra. Walking, sitting, climbing stairs, running, biking, sports, etc. can now be achieved while the user waits for medication activation or surgery.

As discussed above, catheter use, because of the nature of its location, causes most men to become somewhat immobilized due to the pain and discomfort. This can have a major detriment to the quality of life as a sedentary lifestyle is opted to alleviate the pain. This is a major setback as physical activity is critical to an individuals' overall health and well-being. The present invention offers those who have no choice but to use a catheter a better quality of life.

In exemplary embodiments, the present invention may adhere to various universal standards listed as follows, and it may be adapted for use by children and females. The average length of a male catheter is 16" long. There are also varying lengths to accommodate for the different urethral lengths between genders and ages: Pediatric catheters are typically around 10 inches long. Female catheters range 6-8 inches in length. Male/Unisex catheters are usually approximately 16 inches long.

The diameter of the tube (specifically, the external diameter) is determined by a universal color-coding system. This is referred to as a French size or Fr. This is based upon the measure of the external diameter of the tube. In preferred embodiments, the present invention will be used with the Stat-Lock pivoting securement system. This allows for a further range of pain-free movement and additional security that the urinary bag will not detach from the catheter.

Advantageously, the introduction of coiled tubes to the external area of the in-dwelling catheter increases the range of motion for a user due to the expansion and retraction of the coil. This introduction also substantially decreases the friction caused by the in and out movement during daily activities along the urinary tract, reducing trauma and pain that would otherwise be experienced by the user due to prolonged used of the catheter.

These and other features, aspects and advantages of the present invention will become better understood with reference to the following drawings, description, and claims.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, without departing from the scope of this disclosure.

DETAILED DESCRIPTION OF THE INVENTION

Figure 1:
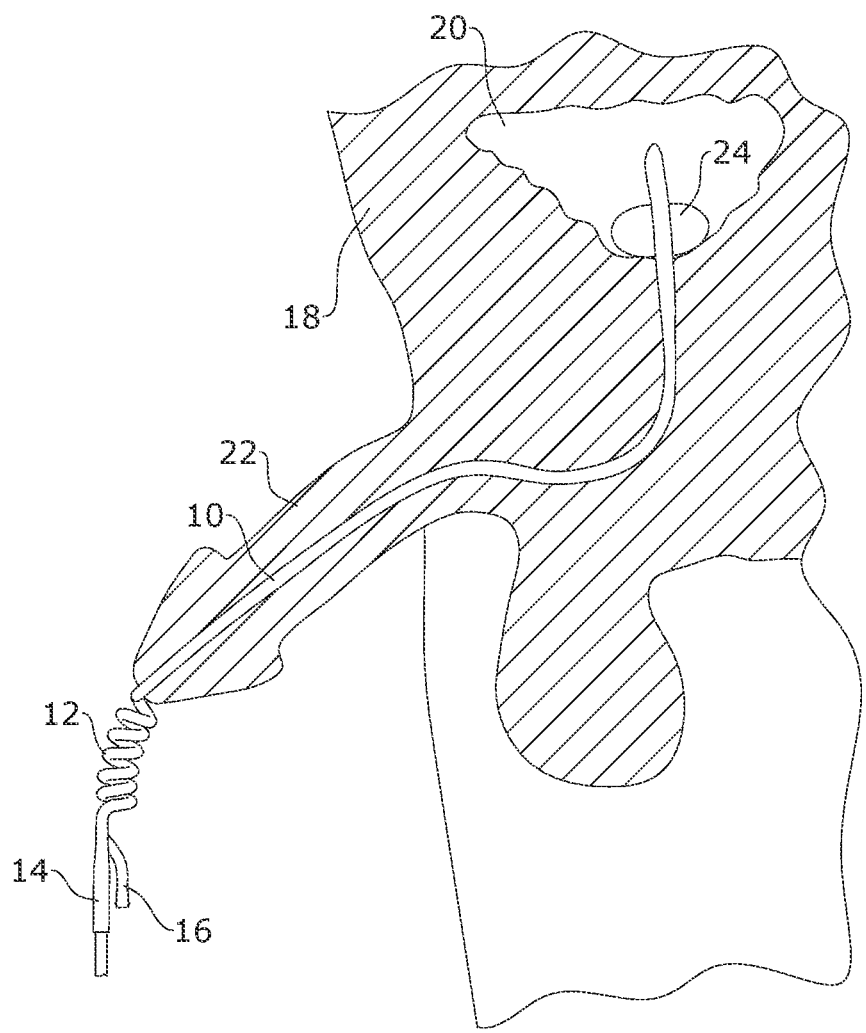
FIG. 1 is a schematic view of an embodiment of the present invention, shown in use.
Figure 2:
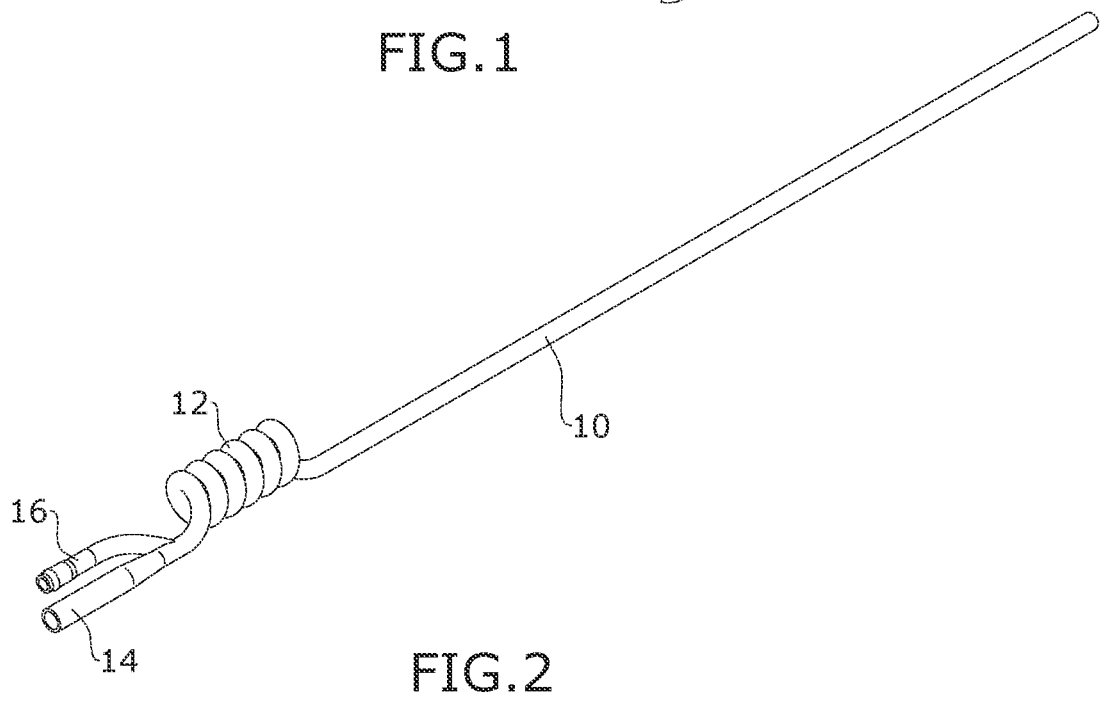
FIG. 2 is a perspective view of the embodiment of the present invention.

The subject disclosure is described with reference to the drawings, wherein like reference numerals are used to refer to like elements throughout. In the following description, for purposes of explanation, numerous specific details are set forth in order to provide a thorough understanding of the present disclosure such that one skilled in the art will be enabled to make and use the present invention. It may be evident, however, that the present disclosure may be practiced without some of these specific details.

Broadly, one embodiment of the present invention is an indwelling catheter with an integrated coil section disposed on an outer side thereof (i.e., the side that does not extend into a user's urethra). Referring to FIGS. 1-6, a catheter 10 is provided substantially in the form of a traditional indwelling urinary catheter in terms of components and functionality. For example, the catheter may include one or more drain ports 14 and an inflator port 1 for filling a balloon 24 (which holds the catheter 10 in position, once inserted into a bladder 20 of a user 18). Insertion is typically done by a medical professional, homecare nurse, or individual under guidelines and directive from a professional specializing in incontinence. This catheter 10 drains urine from the bladder 20 into a bag (not shown) outside the body of the user 18. The catheter 10 has three primary sections, a first section that extends into the urethra and terminates in the bladder 20 of the user, a second section that includes the aforementioned ports 14, 16, and a coil section 12 disposed therebetween.

Advantageously, the coil section 12 is incorporated with the catheter 10 in order to increase its range of motion and, in general, flexibility. The coil may comprise six to eight coiled tubes (and preferably, for proper operation, six coils), approximately 2-2.25 inches in length (in a relaxed/contracted state), added proximal the one or more drain ports 14 and the inflator port 16. The coil section 12, embodied in a manner as described above, offers an unbridled range of motion up to 4.25 inches due to the expansion and retraction. An additional 2-2.25 inches is also added to the overall length of the catheter 10 to compensate for the added coil section 12, allowing for penis erections without obstruction.

With the new advanced coiled design (i.e., the coil section 12) coupled with the traditional features of the indwelling catheter 12, design and performance are improved ten-fold. Embodiments of the present invention now permit a significantly wider range of motion by reducing back and forth friction of the part of the catheter that is inside the urethra that causes restriction of movement. The concept is similar to a suspension on an automobile that absorbs the bumps on a road while the car remains stabilized.

Figure 3:
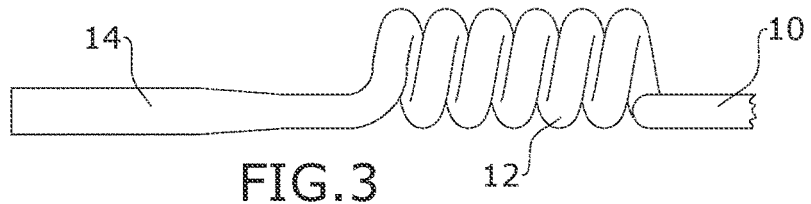
FIG. 3 is a detailed side view of the embodiment of the present invention, showing the coil in an unstretched, non-bent position.
Figure 4:
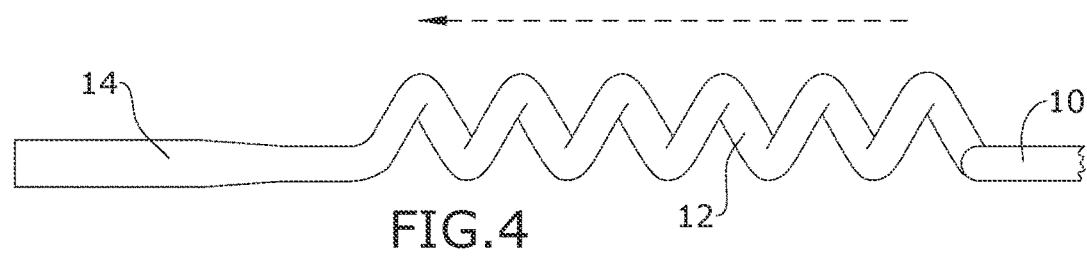
FIG. 4 is a detailed side view of the embodiment of the present invention, showing the coil in a stretched position, with the unstretched position shown in phantom lines for reference.
Figure 5:
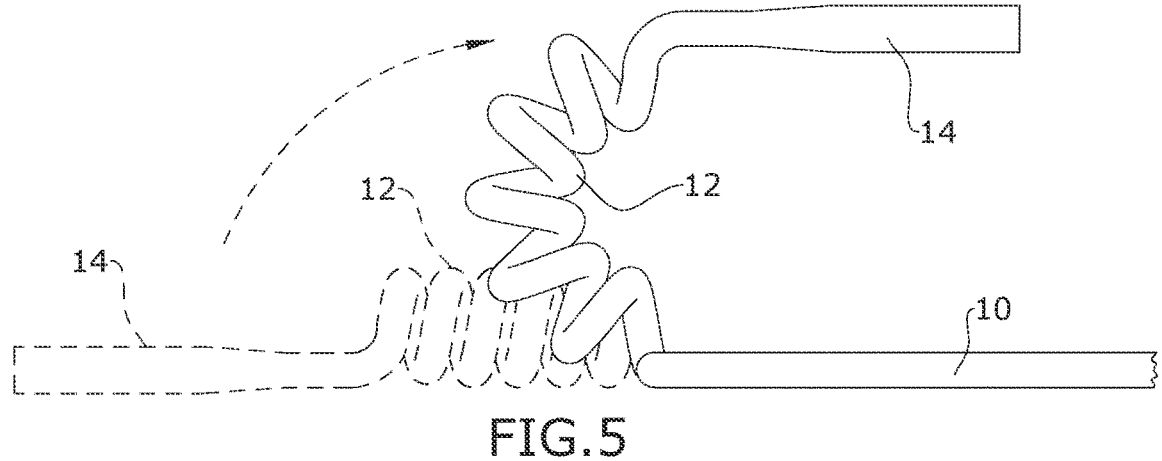
FIG. 5 is a detailed side view of the embodiment of the present invention, showing the coil in a first bent position, with the unbent position shown in phantom lines for reference.
Figure 6:
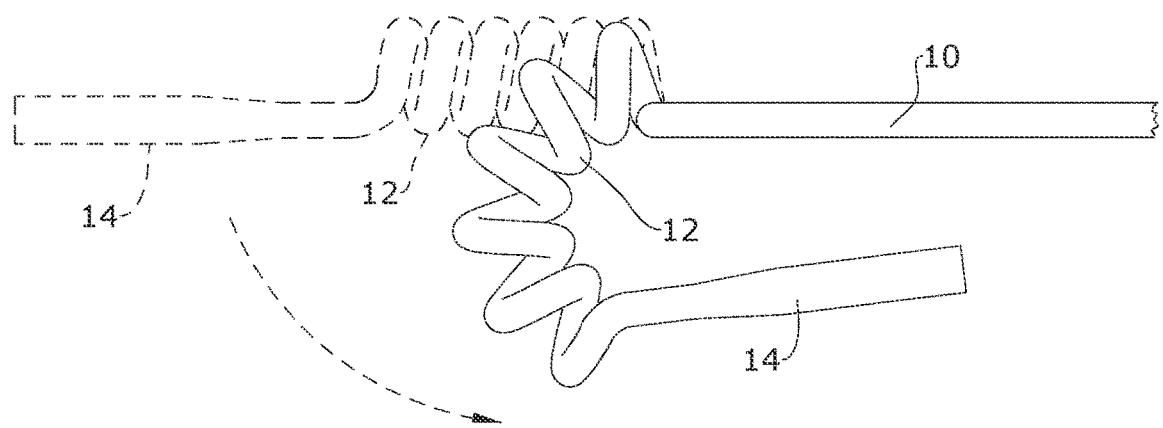
FIG. 6 is a detailed side view of the embodiment of the present invention, showing the coil in a second bent position.

In use, and as shown in FIGS. 3 and 4, the coil section 12 can selectively expand and collapse, based on external forces, just above the urine drainage 14 and balloon 16 port and before the external urethral opening to the traditional/ Foley indwelling catheter design (i.e., the section 12 is, in use, just outside the body of the user 18, as shown in FIG. 1). The internal part of the catheter 10 that is in the urethra/urinary tract is 12 to 14 inches and remains stable due to the coil section 12, thereby minimizing friction causing pain. The kinetic energy, created by a range of motion or ROM from walking, running, biking, etc., is absorbed by the expansion and contraction of the coil section 12, thereby reducing friction (the resistance that one surface or object encounters when moving over another) of the catheter's indwelling portion in the urethra, which is what causes pain. Similarly, as shown in FIGS. 5-6, the coil section 12 permits the catheter 10 to bend approximately 180 degrees in all directions, even further increasing the absorption of external forces on the catheter (and therefore, reducing the stress applied to the indwelling portion of the catheter 10 in the urethra). Residually, this will help to reduce a user's otherwise sedentary lifestyle (borne out of necessity due to discomfort). A major advantage of this embodiment is the simplicity of design. For example, there are no other complicated biasing mechanisms or other structure that would make it more difficult to use, more uncomfortable to use or more likely to break after prolonged usage, not to mention increases costs associated with the production thereof (due to the higher level of complexity of design).

The indwelling catheter 10 with integrated coil section 12 of the present invention may be formed from various appropriate materials, including rubber, latex, silicone, or a combination thereof. In certain embodiments, a combination of soft plastic polymers may be molded to create the external shell and internal tubing of the catheter 10. A rigid plastic polymer may be molded as a cap and fit to the balloon port 16. The soft plastic polymers are procured/formed to create the flexible catheter tube 10, along with the coil section 12. The inner portion of the catheter 10 contains two internal channels, extending through the coil section 12, and ending in two ports 14, 16. The first internal channel leads to the port 14 to drain urine from the bladder. The second internal channel leads to the balloon port 16 used to inflate and deflate the balloon 24 of the catheter that keeps it secure inside the bladder 20. The hard-plastic polymers are procured/formed to create a cap that houses an inflation device and may be molded to the balloon port 16. Any appropriate molding apparatus may be used to produce embodiments described herein.

ADL (Activities of Daily Living) studies measure the joint angles involved in everyday tasks of everyday living. This is especially important for males 50 plus. Basic ADL's include eating, dressing, getting in or out of bed or a chair, taking a shower or bath and using the toilet. ROM (Range of Motion) Functional joint range of motion has been defined as the minimum range of motion (ROM) necessary to perform activities of daily living comfortably and effectively. Using geometry plus the following averages: the male height of 5'9", a leg inseam of 31", length of stride required, divided by 2 (male urinary tract is centered) equals the measurement needed to perform individual activities, the following working coil measurements were calculated to provide adequate range of motion (ROM) for different activities.

1. Standing: typical leg separation angle: 15°; coil retracted length: 2.25 inches
2. Basic ADL (as explained above): typical leg separation angle: 30°; coil working length: 2.75 inches
3. Running, tennis, basketball, swimming, and the like: typical leg separation angle: 45°; coil working length: 3.25 inches
4. Bicycling and hiking: typical leg separation angle: 90°; coil working length: 4.25 inches The application of the coil system 12 of the present invention is the best possible way to allow a range of movement and maintain the integrity and functionality of the existing indwelling catheter. The internal tube structure of a catheter 10 has two channels, sometimes three, that must be adhered to. The large channel is to void urine, the second, smaller channel is to inflate and deflate the balloon for the catheter to remain secure, and when included, a third channel is used for irrigation and flushing of the bladder. In research and development of the present invention, it was determined that any design other than tubular coils 12 would destroy the utility of an indwelling catheter 10.

In conclusion, BPH is anticipated to be the fastest-growing segment with a CAGR of 5.80% It is a very common condition in the aging population. According to the Urology Care Foundation, around half of the men in the age of 51 and 60 years have BPH and up to 90% of the men in the age of 80 years have BPH. Acute urinary retention is a serious complication associated with BPH and requires catheterization of the bladder. The National Association for Continence states that it affects approximately 200 million people worldwide. It also states that one-third of the men and women between the age of 30 and 70 years face a loss of bladder control at some point in their adult life. An indwelling catheter 10 with integrated coil section 12, in accordance with the present invention, will offer a solution to that astonishing number by allowing quality of life for the duration of catheter use.

While one or more preferred embodiments are disclosed, many other implementations will occur to one of ordinary skill in the art and are all within the scope of the invention.

Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

While apparatuses and methods are described in terms of "comprising," "containing," or "including" various components or steps, the apparatuses and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An indwelling catheter comprising:
   an elongated catheter main body defining:
      a first section that is configured to be inserted into a urethra of a human patient through a urethral opening;
      a second section comprising one or more ports and is configured to be disposed outside of the urethra; and
      a flexible coil section that is disposed between the first section and the second section and is configured to be disposed outside of the urethra proximal to the urethral opening, the flexible coil section has a longitudinal length of approximately 2 to 2.25 inches in a contracted position and approximately 4.25 inches in a stretched position, and extends from a distal end at the second section to a proximal end at the first section, and the proximal end is configured to be directly adjacent to the urethra opening of the urethra when the first section is arranged within the urethra, wherein the flexible coil section is configured to expand and bend based on a kinetic energy of an external force applied to the second section and the flexible coil section due to a range of motion of the human patient, contract toward a contracted position in a relaxed state based on a relaxation of the range of motion of the human patient, and absorb, by expansion and contraction, the kinetic energy.

2. The indwelling catheter of claim 1, wherein the flexible coil section comprises between six and eight coiled tubes.

3. The indwelling catheter of claim 2, wherein the flexible coil section comprises six coiled tubes.

4. The indwelling catheter of claim 1, wherein the flexible coil section is a substantially circular helix in shape.

5. The indwelling catheter of claim 1, wherein the flexible coil section comprises a plurality of flexibly coiled tubes.

6. The indwelling catheter of claim 1, wherein the flexible coil section is configured to bend up to approximately 180 degrees.

7. The indwelling catheter of claim 1, further comprising a plurality of channels extending from the first section, through the flexible coil section, and to the second section.

8. The indwelling catheter of claim 7, wherein each channel of the plurality of channels is operably associated with a respective port of the one or more ports.

9. The indwelling catheter of claim 1, wherein the first section extends from the flexible coil section to a terminal end configured to be positioned within a bladder of the human patient, the first section having a length between about 12 to about 14 inches.

10. The indwelling catheter of claim 9, wherein the first section, second section, and flexible coil section are integrally formed as a unitary component.

11. The indwelling catheter of claim 10, wherein a length between the terminal end of the first section within the bladder and a proximal end of the second section where the flexible coil section interfaces with the second section is between 14 inches and 16.25 inches when the flexible coil section is in a contracted position.

12. The indwelling catheter of claim 11, wherein the first section, second section, and coil section do not include another biasing mechanism.

13. A method of catheterization comprising:
inserting a first section of an elongated catheter main body into a urethral opening of a urethra of a human patient through a urethral opening, the elongated catheter main body comprising:
the first section that is configured to be inserted into the urethra of the human patient through the urethral opening;
a second section comprising one or more ports and configured to be disposed outside of the urethra; and
a flexible coil section that is disposed between the first section and the second section and configured to expand and bend based on a kinetic energy of external forces applied to the second section and the flexible coil section due to a range of motion of the human patient, and contract toward a contracted position in a relaxed state based on a relaxation of the range of motion of the human patient, and absorb, by expansion and contraction, the kinetic energy, the flexible coil section having a longitudinal length of approximately 2 to 2.25 inches in a contracted configuration and approximately 4.25 inches in an expanded configuration; and inserting the first section through the urethra such that the first section extends to a bladder of the human patient and the flexible coil section disposed outside of the urethra directly adjacent to the urethral opening.

14. The method of claim 13, further comprising:
applying an external force to the second section due to a range of motion of the human patient;
expanding the flexible coil section away from a contracted configuration and toward an expanded configuration based on kinetic energy of the external force;
absorbing, by the flexible coil section, a portion of the kinetic energy of the external force;
relieving the external force based on a relaxation of the range of motion of the human patient; and
permitting the flexible coil section to contract toward the contracted configuration.

15. The method of claim 13, wherein the first section is between about 12 to about 14 inches in length between a terminal end of the first section within the bladder and the flexible coil section.

16. The method of claim 13, further comprising one or more of:
fluidically connecting a collection bag to a first port of a first channel defined in the elongated catheter main body extending from the first section, through the flexible coil section, to the second section;
fluidically connecting an inflator to a second port of a second channel defined in the elongated catheter main body extending from the first section, through the flexible coil section, to a balloon at a distal end of the second section;
inflating, by the inflator, the balloon; and
bending, by external force, the flexible coil section up to approximately 180 degrees.

* * * * *